United States Patent [19]

Beck et al.

[11] Patent Number: 5,118,880
[45] Date of Patent: Jun. 2, 1992

[54] METHOD OF PREPARING 2-BROMO-4,6-DINITROMESITYLENE

[75] Inventors: William A. Beck, Middletown; David P. Higley, Wilmington, both of Del.; John R. Tyndall, Pisgah Forest, N.C.

[73] Assignee: E. I. Du Pont de Nemours & Co., Wilmington, Del.

[21] Appl. No.: 720,679

[22] Filed: Jun. 25, 1991

[51] Int. Cl.$^5$ .............................................. C07C 205/12
[52] U.S. Cl. .................................... 568/940; 568/937; 568/939
[58] Field of Search ............... 568/939, 940, 937, 924, 568/927, 932, 933, 934, 936

[56] References Cited

U.S. PATENT DOCUMENTS 2,314,212  3/1943  Hennion ........................... 568/940 X
2,934,571  4/1960  Bonetti ............................. 568/939 X
3,180,900  4/1965  Sparks .............................. 568/937
3,221,062  11/1965  Wright ............................. 568/940 X

OTHER PUBLICATIONS

Urbanaski, T. "Chemistry and Technology of Explosives" vol. 1, p. 413, 1964, Permagon Press.
Topochiev, A. V., "Nitration of Hydrocarbons and Other Organic Compounds", p. 158, 1959, Permagon Press.

Primary Examiner—John S. Maples
Assistant Examiner—C. Sayala

[57] ABSTRACT

A method of preparing 2-bromo-4,6-dinitromesitylene having only small amounts of impurities, by first mixing fuming sulfuric acid with bromomesitylene, and then adding concentrated nitric acid.

10 Claims, No Drawings

METHOD OF PREPARING 2-BROMO-4,6-DINITROMESITYLENE

1. FIELD OF THE INVENTION

This invention relates to a method of preparing bromodinitrocompounds. More particularly it pertains to a method of preparing 2-bromo-4,6-dinitromesitylene.

2. BACKGROUND OF THE INVENTION 2-bromo-4,6-dinitromesitylene may be used as a starting material to form a number of compounds, such as for example 2-perfluoroalkyl-4,6-diaminomesitylene, which in turn may be used as one of the main constituents in polyamides, polyimides, urethanes,ureas, and the like.

2-bromo-4,6-dinitromesitylene has been prepared so far by reacting nitric acid or a mixture of fuming sulfuric and nitric acids with bromomesitylene. Such preparations are shown for example in very old as well as more recent references, such as "Fittig and Storer, *Liebigs Ann. Chem.*, 147, 1-11 (1868)", "Suessenguth, *Liebigs Ann. Chem.*, 215, 242-252 (1882)", and "Adams and Miller, *J. Amer. Chem. Soc.*, 62, 53-56 (1940)."

The following is translated from Fittig and Storer (p. 8): "By pouring fuming nitric acid over bromomesitylene at ambient temperature and after short standing, it is converted into the (title) compound, which through washing with water and recrystallization with alcohol is easily purified. It crystallizes in fine, colorless needles, which dissolve little in cold alcohol, easier in hot alcohol, yet are much less soluble than the starting compound. Its melting point is 189°-190° C. Under warming, the compound develops a genuine musk smell."

| Analysis: | | Calculated | Found |
|---|---|---|---|
| C9 | 108 | 37.37% | 37.16% |
| H9 | 9 | 3.11 | 3.29 |
| Br | 80 | 27.68 | 27. |
| 2 NO$_2$ | 92 | 1.84 | — |
| | 289 | 100.00 | |

This preparation appears to be simple and leading to a pure product, since there are only two positions in the aromatic ring of bromomesitylene, which are open for substitution by nitro groups. Simple elemental analysis, indicates the reaction to be clean and straightforward. However, more careful examination of this reaction reveals it to be considerably more complicated.

Depending on how the reaction is conducted, a number of undesirable by-products, such as 2,4,6-trinitromesitylene, 2,4-dibromomesitylene, and 2,4-dibromo-6-nitromesitylene, are formed. Some of these by-products are extremely difficult to separate, because they cocrystallize with the desired product, even upon repeated recrystallization from a variety of solvents. These by-products may also prove to be catastrophic to polymers intended to be made from derivatives of the main product (dinitro compounds) after hydrogenation (diamines), since monoamine derivatives will serve as chain terminators, and triamine derivatives will serve as crosslinkers. Thus, expensive procedures, such as repeated crystallizations, sublimations, and the like are needed for purifying the products obtained in subsequent conversions of impure 2-bromo-4,6-dinitromesitylene, to free these products from undesirable impurities.

In contrast to previous attempts, considerably purer 2-bromo-4,6-dinitromesitylene may be prepared according to the methods of the present invention.

3. SUMMARY OF THE INVENTION

The instant invention pertains to a method of preparing 2-bromo-4,6-dinitromesitylene comprising the steps of:

(a) mixing fuming sulfuric acid with 2-bromomesitylene; and (b) mixing nitric acid with the mixture of step (a).

Preferably, in step (a), the 2-bromomesitylene is added to the fuming sulfuric acid at a temperature lower than 30° C. preferably between 10° C. and 20° C., with vigorous stirring.

The nitric acid is preferably in the form of an aqueous solution containing nitric acid in excess of 70% by weight, and more preferably at a concentration of substantially 90%. Preferably the temperature during nitration is maintained in the range of 30°-50° C., and more preferably in the range of 35°-45° C.

4. DETAILED DESCRIPTION OF THE INVENTION

The instant invention pertains to a method of preparing 2-bromo-4,6-dinitromesitylene.

The preparation of 2-bromo-4,6-dinitromesitylene by reacting nitric acid or a mixture of nitric acid and fuming sulfuric acid with bromomesitylene appears to be simple, since there are only two places in the bromomesitylene where hydrogen atoms may be easily replaced by nitro groups. However, in practice, this reaction is considerably more complicated.

As aforementioned, depending on how the reaction is conducted, a number of undesirable by-products, such as 2,4,6-trinitromesitylene, 2,4-dibromomesitylene, and 2,4-dibromo-6-nitromesitylene, are formed, which are difficult to distinguish and separate, since they seem to have similar crystalline characteristics. The by-products of these reactions may sometimes prove to be catastrophic to polymers intended to be made from the main product (dinitrocompound) after hydrogenation (diamine), since monoamines will serve as chain terminators, and triamines will serve as crosslinkers. Thus, expensive procedures, such as repeated crystallizations, sublimations, and the like are needed for purifying the product and remove the undesirable impurities.

In contrast to previous attempts, considerably purer 2-bromo-4,6-dinitromesitylene may be prepared according to the method of the present invention. It was very unexpected to find out that if the sulfuric acid and the nitric acid are not mixed simultaneously with the bromomesitylene, but only the sulfuric acid is mixed first with bromomesitylene, and the nitric acid is mixed then, the reaction yields a considerably purer product. One would expect that free water might be the culprit in the production of various by-products. By mixing first the fuming sulfuric acid with the fuming nitric acid, all the water coming along with the nitric acid is reacted with the free sulfur trioxide of the fuming sulfuric acid, and thus, this is the technique one would follow to assure absence of water, and purer product. However, as already mentioned, Applicants found that mixing first the bromomesitylene with the fuming sulfuric acid and then adding the nitric acid, produces a considerably purer product, which is not concurrent with the above logic. Applicants may not provide any proven explanation on why this is so. Only pure speculations may be made, such as for example, that sulfonation may occur first with subsequent replacement of the sulfonic groups by nitro groups, and for some unclear reason this interferes with the production of undesirable products.

Another speculation is that 2-bromomesitylene, when added to nitric acid or to a mixture of nitric and sulfuric acids, undergoes a rapid bromine-transfer reaction to form a significant portion of dibromomesitylene. This may occur as the major process when reaction conditions are not sufficiently severe to effect nitration to any considerable extent. When conditions are such as to effect nitration, the bromine transfer reaction appears to occur competitively with nitration, to an extent such that undesirable quantities of 2,4-dibromo-6-nitromesitylene are found in the final product. This compound may arise from formation of 2,4-dibromomesitylene by bromine transfer, followed by nitration of the dibromo compound.

It may also be speculated that the bromine transfer reaction and subsequent conversion to final products may occur in one of two ways:

(1) 2-Bromomesitylene is protonated in strong acid medium at the carbon atom bearing bromine, to give an intermediate organic cation which can serve as a bromonium ion donor. Loss of bromonium ion (Br+) from this cation may give a molecule of mesitylene, which upon nitration may generate 2,4,6-trinitromesitylene. The loss of bromonium ion from the intermediate organic cation may actually involve its transfer to another molecule of 2-bromomesitylene, with the result that a new organic cation is formed, this one bearing two bromine atoms. Subsequent loss of a proton from this new organic cation will generate a molecule of 2,4-dibromomesitylene, which as mentioned above can then be nitrated to form 2,4-dibromo-6-nitromesitylene.

(2) In the presence of nitric acid, 2-bromomesitylene may be attacked by nitronium ion at the carbon bearing the bromine, to give an intermediate organic cation which can serve as a bromonium ion donor. Loss of bromonium ion may in this case leave a molecule of 2-nitromesitylene, further nitration of which may give 2,4,6-trinitromesitylene. The bromonium ion which is lost may be accepted by another molecule of 2-bromomesitylene, giving rise to 2,4-dibromomesitylene as described for (1) above.

Both of these proposed mechanisms may explain the appearance of the observed by-products, 2,4,6-trinitromesitylene and 2,4-dibromo-6-nitromesitylene, but nevertheless are highly speculative. In addition, this does not explain why addition of 2-bromomesitylene to fuming sulfuric acid, followed by the addition of nitric acid to the resulting mixture, results in the elimination of the bromine-transfer process. One may go on speculating that in the latter case all of the following conditions are probably met:

Sulfonation of 2-bromomesitylene may occur under these conditions, to give 3-bromo-2,4,6-trimethylbenzenesulfonic acid much faster than bromine transfer may occur;

The benzenesulfonic acid derivative may be deactivated so far as any bromine transfer process is concerned;

Upon addition of nitric acid, the benzenesulfonic acid derivative may be attacked by nitronium ion at the carbon bearing the sulfonic acid group; a proton may be lost from the sulfonic acid group in the resulting intermediate, then a molecule of sulfur trioxide may be lost, leaving a molecule of 2-bromo-4-nitromesitylene;

The resulting 2-bromo-4-nitromesitylene may be sufficiently deactivated by the nitro group that it cannot undergo the bromine transfer process, but instead may undergo nitration to form the final, desired product, 2-bromo-4,6-dinitromesitylene.

The above schemes are of course extremely speculative and should be considered as such with regard to this invention.

On the basis of the results from the experiments shown in the Examples, one may conclude that under ordinary nitration conditions, using 90% fuming nitric acid (Examples 1 and 2), 80% nitric acid (Example 3), or mixed (fuming nitric and sulfuric) acids (Example 4), there occurs an unexpected disproportionation of 2-bromomesitylene to form substantial quantities of mesitylene and 2,4-dibromomesitylene. Nitration occurring concurrent with this disproportionation leads to the formation of 2,4,6-trinitromesitylene and 2,4-dibromo-6-nitromesitylene, along with the desired 2-bromo-4,6-dinitromesitylene. Subsequent repeated recrystallizations of the product (Example 1) afford a material which, by its highly crystalline appearance and sharp melting point, might be judged to be of high purity, but which by careful analysis is shown to contain only about 87% by weight of the desired product. It appears that preparation of this compound in the pure state has never been accomplished until now.

Example A illustrates a highly preferred embodiment of this invention, where fuming sulfuric acid is mixed first with 2-bromomesitylene, and then fuming nitric acid is added to result in a nitrated product substantially free from troublesome by-products.

Although concentrated nitric acid may be used in place of fuming nitric acid in the preparation of 2-bromo-4,6-dinitromesitylene (Example B) according to the method of this invention, the resulting product is not as pure as that obtained under the conditions of the preferred embodiment.

If concentrated sulfuric acid is used in place of the fuming sulfuric acid (Example C), the resulting product has impurities. This indicates that water is unfavorable in producing 2-bromo-4,6-dinitromesitylene of high purity, regardless of the order of addition of the reagents.

Finally, when the nitration step is carried out at temperatures below 30° C. (Example D), a poorer yield of product is obtained. The purity of this product, though quite high, is nevertheless inferior to that obtained at a higher nitration temperatures, as shown in Example A.

GLOSSARY

6FDA: 2,2'-bis(3,4-dicarboxyphenyl)hexafluoropropane
GC: Gas Chromatography
GPC: Gel Permeation Chromatography
NMP: N-methyl-2-pyrrolidone
NMR: Nuclear Magnetic Resonance
Rf8DAM: 2-Perfluorooctyl-4,6-diaminomesitylene In the Examples below all parts and percentages are given by weight unless otherwise stated. The examples are given for illustration purposes only, and should not be construed as restricting the present invention as claimed.

Examples Relative to the Present Invention

EXAMPLE A

Preferred Method

In a 250-ml flask, equipped with a mechanical stirrer, thermometer, and addition funnel, was placed 75 ml of fuming sulfuric acid (20% $SO_3$). To the stirred acid was added slowly 15.3 ml (19.9 g, 100 mmol) of 2-bromomesitylene, while the temperature of the mixture was kept under 25° C. by cooling with an ice bath. There was then added dropwise to the stirred mixture 17.3 ml of fuming 90% nitric acid, while the reaction temperature was maintained within the range of 25° to 38 ° C. by continued cooling. Upon completion of this addition, the mixture was stirred for one hour at a temperature of 40° C. The resulting thick slurry was rinsed with water from the flask onto ice. The solid product was collected by suction filtration, washed with water, and air dried. Analysis of this material showed it to consist of the desired product, 2-bromo-4,6-dinitromesitylene, in a purity of 96.0%, along with small amounts of unidentified impurities; neither 2,4,6-trinitromesitylene nor 2,4-dibromo-6-nitromesitylene was detected. The weight of crude product was 26.0 g; corrected for the measured purity, this corresponds to a yield of 25.0 g (87 mmol, 87% of theory) of the desired material.

Recrystallization of the crude product from acetonitrile gave needles melting at 197°-198° C., for which gas chromatographic analysis (GC) indicated a purity of 98.4%. The structure and purity of this material were confirmed by proton nmr analysis. This result is surprising, in that the formation of troublesome by-products—which could not be removed by repeated recrystallization of crude product—has been entirely eliminated by the simple expedient of combining the organic substrate with fuming sulfuric acid prior to the addition of nitric acid. A valuable intermediate is thereby obtained by a practical method, and in a highly pure state, such that it can be used as a starting material for the preparation of other compounds of interest, without complicating the subsequent purification of such compounds through the introduction of undesirable impurities.

EXAMPLE B

The same general procedure as described for the method of Example A was followed, but using concentrated (rather than fuming) nitric acid:

To a 37.5-ml portion of fuming sulfuric acid (27-33% $SO_3$) was added dropwise, with stirring, 7.6 ml (9.9 g, 50 mmol) of 2-bromomesitylene. The temperature of the reaction mixture was kept below 20° C. during this addition by cooling with an ice-water bath. After the addition of bromomesitylene was completed, 12.5 ml of concentrated (70%) nitric acid was added dropwise, while the reaction temperature was maintained at 35°-40° C. Following this addition the reaction mixture was stirred for 30 minutes longer while its temperature was maintained at about 35° C. The mixture was allowed to cool to room temperature, then poured into 400 ml of ice-water. The solid product was collected by suction filtration, washed with water, and air dried. Analysis of this product by gas chromatography (GC) showed it to consist of 2-bromo-4,6-dinitromesitylene, 93.3%, plus two unidentified minor components with substantially greater retention times. However, impurities such as 2,4-dinitromesitylene, 2,4-dibromo-6-nitromesitylene, or 2,4,6-trinitromesitylene, which are formed by conventional methods were not observed.

One may conclude that although concentrated nitric acid may be used in place of fuming nitric acid in the preparation of 2-bromo-4,6-dinitromesitylene according to the method of this invention, the resulting product is not as pure as that obtained under the conditions of the preferred embodiment.

EXAMPLE C

The same general procedure as described for the method of Example A was followed, but using concentrated (rather than fuming) sulfuric and nitric acids:

To a 75-ml portion of concentrated sulfuric acid was added dropwise, with stirring, 15.3 ml (19.9 g, 0.10 mol) of 2-bromomesitylene. The temperature of the reaction mixture was kept below 25° C. during this addition by cooling with an ice-water bath. After the addition of bromomesitylene was completed, 25 ml of concentrated (70%) nitric acid was added dropwise, also at a controlled reaction temperature of less than 25° C. Following this addition the reaction mixture was stirred for two hours longer, while its temperature was maintained below 30° C. The mixture was then poured over ice, and the solid product was collected by suction filtration and air dried. Analysis of the crude product by gas chromatography (GC) showed it to consist of 2-bromo-4,6-dinitromesitylene, 80.3%; 2,4-dibromomesitylene, 8.8%; dinitromesitylene, 1.2%; 1,4-dibromo-6-nitromesitylene, 4.5%; trinitromesitylene, 3.1%; and traces of several unidentified impurities.

This indicates that water is unfavorable in producing 2-bromo-4,6-dinitromesitylene of high purity, regardless of the order of addition of the reagents.

EXAMPLE D

Example showing the effect of lower nitration temperature:

To 225 ml of fuming sulfuric acid (20% $SO_3$) was added slowly, with stirring and cooling to maintain the reaction temperature below 25° C., 45.9 ml (59.7 g, 0.30 mol) of 2-bromomesitylene. Following this addition, with continued stirring there was added dropwise 52.5 ml of fuming (90%) nitric acid, while the temperature of the reaction mixture was kept below 30° C. by continued cooling. The mixture was stirred for one hour at 25°-30° C. following completion of the nitric acid addition, then poured into ice-water. The solid product was collected by suction filtration, washed with water, and air dried to yield 36 g of material which was shown by GC analysis to consist of 97.5% of the desired compound, 2-bromo-4,6-dinitromesitylene. Corrected for measured purity, the yield was 35.1 g (0.12 mol), or 40% of theory.

This indicates that when the nitration step is carried out at temperatures below 30° C., a poorer yield of product is obtained; and that the purity of this product, though quite high, is nevertheless inferior to that obtained at a higher nitration temperature, as shown in Example A.

Comparative Examples

EXAMPLE 1

A 290-g (1.5-mol) quantity of 2-bromomesitylene was added during about one hour, with stirring, to 500 ml of cold fuming 90% nitric acid; the temperature of the reaction mixture was maintained at less than 0° C. throughout the addition. Stirring was continued for one hour at 0° C. after this addition. The product mixture was then poured over ice, and the solid product was collected by suction filtration and washed with copious amounts of water. After air drying, the product was recrystallized from cyclohexane, and subsequently from toluene, giving fine needles with m.p. 197°–198° C.

Analysis of this product by gas chromatography-mass spectroscopy revealed it to consist of 2,4-dibromo-6-nitromesitylene, 11.3%; 2-bromo-4,6-dinitromesitylene, 86.0%; and 2,4,6- trinitromesitylene, 2.4%. (Percentages are obtained from GC peak integration with flame-ionization detection, and reflect approximate weight percent).

A portion of the twice-recrystallized sample was recrystallized yet again, from absolute ethanol, to obtain fine, colorless needles, m.p. 195°–197° C. Analysis by GC indicated this to be composed of 2,4-dibromo-6-nitromesitylene, 9.8%; 2-bromo-4,6-dinitromesitylene, 87.6%; and 2,4,6-trinitromesitylene, 2.6%. The same sample was analyzed by proton nmr (CHCl$_3$-d solution). Interpretation and integration of the resulting spectrum, and appropriate calculations to convert measured mole ratios to weight percentages, led to the conclusion that the sample contained, by weight, 2,4-dibromo-6-nitromesitylene, 10.8%; 2-bromo-4,6-dinitromesitylene, 86.6%; and 2,4,6-trinitromesitylene, 2.6%.

EXAMPLE 2

In a 250-ml flask, equipped with a thermometer, stirrer, and addition funnel, was placed 50 ml of fuming 90% nitric acid. With high-speed agitation, there was then added slowly from the addition funnel 22.3 ml (29.0 g, 146 mmol) of 2-bromomesitylene, while the reaction temperature was maintained at 25°–30° C. by means of an ice bath. The mixture was stirred for an additional hour after completion of addition, then poured into water. The solid product was collected by filtration; washed with water, then with hexane; and air dried to give 23.3 g of product. Analysis of this material by GC showed it to consist of 2,4-dibromomesitylene, 4.6%; 2,4-dibromo-6-nitromesitylene, 8.8%; 2-bromo-4,6-dinitromesitylene, 82.8%; and trace quantities of several unidentified components.

Solvent was removed from the hexane solution from the product washing described above, leaving 27 g of solid residue. Analysis of this material by GC showed it to be composed of 2,4-dibromomesitylene, 54.9%; 2,4-dibromo-6-nitromesitylene, 8.3%; 2-bromo-4,6-dinitromesitylene, 16.7%; and several unidentified components.

EXAMPLE 3

In a 250-ml flask, equipped with a mechanical stirrer, thermometer, and addition funnel, was placed 9.3 ml of distilled water. The flask was cooled with an ice bath, and 50 ml of 90% fuming nitric acid was added. To the cold 80% nitric acid thus formed, there was then added dropwise from the addition funnel 22.3 ml (29.0 g, 146 mmol) of 2-bromomesitylene, during a one-hour interval, with stirring and continued cooling to maintain the reaction temperature below 10° C. After completion of this addition the mixture was stirred for one hour longer, while its temperature was kept below 10° C. by continued cooling.

The reaction mixture was poured over ice, and the solid product was collected by suction filtration and washed with water. It was then washed with hexane, in which it proved to be readily soluble. The resulting hexane solution was combined with a portion of methyl t-butyl ether, washed with water, and dried over anhydrous magnesium sulfate. The major isolated product, obtained by concentration and cooling of this solution, was identified by GC analysis as 2,4-dibromomesitylene.

EXAMPLE 4

In a 250-ml flask, equipped with a mechanical stirrer, thermometer, and addition funnel, were combined 25 ml each of 90% fuming nitric acid and fuming sulfuric acid (20% SO$_3$). To the stirred mixture was then added dropwise from the addition funnel, during a one-hour interval, 15.3 ml (19.9 g, 100 mmol) of 2-bromomesitylene. A reaction temperature of 40° C. was maintained during this addition, and during a further one-hour interval following completion of addition, while rapid stirring was continued. The reaction mixture was then poured over ice, and the precipitated solids were collected by suction filtration, washed with water and hexane, and dried. Thus obtained was 25.3 g of product, which by GC analysis was shown to consist of 2,4,6-trinitromesitylene, 13%; 2,4-dibromomesitylene, 1.8%; 2,4-dibromo-6-nitromesitylene, 10%; and 2-bromo-4,6-dinitromesitylene, 71.5%.

EXAMPLE 5

In this Example, the preparation of 2-bromo-4,6-dinitromesitylene was duplicated according to the instructions given by the aforementioned reference of R. Fittig and J. Storer, as follows:

To three grams of 2-bromomesitylene in a 35-ml round-bottom flask was cautiously added, with stirring, 10 ml of fuming nitric acid. The mixture was stirred for about 45 min following completion of this addition, and then was poured into 200 ml of water. The precipitated solid was collected by suction filtration and air dried. Analysis of the resulting product by gas chromatography (GC) showed it to consist of 2-bromo-4,6-dinitromesitylene, 65.8%; 2,4-dinitromesitylene, 13.1%; 2,4-dibromo-6-nitromesitylene, 16.6%; 2,4,6-trinitromesitylene, 3.8%; and traces of unidentified components. (Percentages given correspond to relative peak areas in the gas chromatogram, and reflect approximate weight concentrations). The crude product was recrystallized from ethyl alcohol to give fine, colorless needles. Analysis of the purified product by gas chromatography showed it to consist of 2-bromo-4,6-dinitromesitylene, 74.6%; 2,4-dinitromesitylene, 2.9%; 2,4-dibromo-6-nitromesitylene, 18.3%; and 2,4,6-trinitromesitylene, 4.2%.

On the basis of this experiment, one may conclude that the procedure described by Fittig and Storer results in a very impure product. One may further conclude that although recrystallization from alcohol serves to remove a large portion of the 2,4-dinitromesitylene impurity, the other impurities remain in the recrystallized product in virtually the same proportions, relative to the desired compound, as in the crude reaction product.

Examples of Compounds Made From 2-Bromo-4,6-Dinitromesitylene

EXAMPLE I

Preparation of 2-Perfluorooctyl-4,6-dinitromesitylene

A one-liter flask is flushed with argon and charged with 146.3 g (0.268 mole) of 1-iodoperfluorooctane, 34.1 g (0.536 mole) of copper powder, and 400 ml of dimethylsulfoxide. Under an argon atmosphere, the mixture is stirred and heated to about 100° C., and held at that temperature for 1.25 hour to effect conversion of the 1-iodoperfluorooctane to perfluorooctyl copper(I).

The reaction mixture is cooled to below 70° C., and to it is added 55.0 g (0.19 mole) of 2-bromo-4,5-dinitromesitylene. The mixture is heated overnight at about 70° C., under argon, with continued stirring. A 500-ml portion of water, heated to 60° C., is then added, and the resulting mixture is filtered. The solids are extracted thoroughly with methylene chloride and 1,1,2-trichlorotrifluoroethane. The combined organic extracts are washed with water and dilute sodium bisulfite solution, dried over magnesium sulfate, and the solvent is removed by rotary evaporation at reduced pressure, to leave crude 2-perfluorooctyl-4,6-dinitromesitylene. This is recrystallized from methanol and acetone to give purified product.

EXAMPLE II

Preparation of 2-Perfluorooctyl-4,6-diaminomesitylene

A 76.9-g (0.122-mole) portion of 2-perfluorooctyl-4,6-dinitromesitylene (prepared as described in Example I) is combined with 600 ml of anhydrous ethyl alcohol and 7.6 g of 5% palladium on carbon. The mixture is charged into an autoclave, then heated at 100° C. for seven hours while agitating under a hydrogen pressure of 500 psig. The hydrogenation mixture is cooled and filtered, and solvent is removed from the filtrate by rotary evaporation at reduced pressure to leave a residue of crude product. This is digested in hot hexane, treated with decolorizing charcoal, filtered, and the solution cooled to obtain crystalline product, 2-perfluorooctyl-4,6-diaminomesitylene.

EXAMPLE III

Preparation of 6FDA/Rf8DAM polyimide

Into a 100 ml reaction kettle equipped with a mechanical stirrer, a Dean-Stark trap, and a nitrogen inlet and outlet, are charged 3.5100 g (7.9012 mmoles) 6 FDA (2,2'-bis(3,4-dicarboxyphenyl)hexafluoropropane) and 4.4900 g (7.9012 mmoles) of Rf8DAM (2-perfluorooctyl-4,6-diaminomesitylene). These monomers are then dissolved in 24 ml of anhydrous NMP (N-methyl-2-pyrrolidone) and 12 ml of m-xylene. The Dean-Stark trap is also filled with m-xylene. After dissolution of the monomers, the solution is heated via a silicone oil bath to reflux the m-xylene (bath temperature ~190° C.) in order to azeotropically remove the water generated by imidization. The reaction is allowed to proceed overnight. Upon cooling, a higher viscosity phase separates from the reaction solvent. Addition of a small amount of chloroform and heating to ~80° C. rehomogenizes the solution which is then precipitated into methanol. The polymer is then redissolved in chloroform, precipitated into methanol, isolated by filtration and dried under vacuum with nitrogen bleed.

The purified polymer may be redissolved in NMP or other solvent, and cast onto a substrate, such as for example a silicon wafer. After evaporation of the solvent, an excellent coating is left on the substrate. In addition to coatings, free films may also be produced by procedures well known to the art.

What is claimed is:

1. A method of making 2-bromo-4,6-dinitromesitylene comprising the steps of:
   (a) mixing fuming sulfuric acid with 2-bromomesitylene; and
   (b) mixing nitric acid present in a concentration higher than 70% by weight with the mixture of step (a).

2. A method of making 2-bromo-4,6-dinitromesitylene as defined in claim 1, wherein the 2-bromomesitylene is added into the fuming sulfuric acid.

3. A method of making 2-bromo-4,6-dinitromesitylene as defined in claim 2, wherein the mixture of the fuming sulfuric acid with 2-bromomesitylene is kept at a temperature below 30° C. during mixing of the sulfuric acid with the 2-bromomesitylene.

4. A method of making 2-bromo-4,6-dinitromesitylene as defined in claim 3, wherein the mixture of the fuming sulfuric acid with 2-bromomesitylene is kept at a temperature in the range of 10° to 20° C. during mixing the sulfuric acid with the 2-bromomesitylene.

5. A method of making 2-bromo-4,6-dinitromesitylene as defined in claim 1, wherein the fuming sulfuric acid contains $SO_3$ in the range of 10–30% by weight.

6. A method of making 2-bromo-4,6-dinitromesitylene as defined in claim 5, wherein the fuming sulfuric acid has a concentration of free $SO_3$ higher than 20% by weight.

7. A method of making 2-bromo-4,6-dinitromesitylene as defined in claim 1, wherein the nitric acid is contained in water at a concentration of substantially 90% by weight.

8. A method of making 2-bromo-4,6-dinitromesitylene as defined in claim 1, further comprising the steps of stirring the mixture of step (b) with ice, separating by filtration and washing with water the resulting 2-bromo-4,6-dinitromesitylene.

9. A method of making 2-bromo-4 6-dinitromesitylene as defined in claim 8, further comprising the step of recrystallizing the 2-bromo-4,6-dinitromesitylene.

10. A method of making 2-bromo-4,6-dinitromesitylene as defined in claim 1 wherein the nitric acid is fuming nitric acid.

* * * * *